(12) United States Patent
Lopez et al.

(10) Patent No.: US 9,260,012 B2
(45) Date of Patent: Feb. 16, 2016

(54) BEVERAGE DISGUISE FOR HAND HELD BREATHALYZER INTERFACE OF IGNITION INTERLOCK DEVICE

(71) Applicant: Mesa Digital, LLC, Albuquerque, NM (US)

(72) Inventors: Davin E. Lopez, Las Cruces, NM (US); Luis M. Ortiz, Albuquerque, NM (US)

(73) Assignee: Mesa Digital, LLC, Albuquerque, NM (US)

( * ) Notice: Subject to any disclaimer, the term of this patent is extended or adjusted under 35 U.S.C. 154(b) by 296 days.

(21) Appl. No.: 14/061,314

(22) Filed: Oct. 23, 2013

(65) Prior Publication Data

US 2014/0041955 A1 Feb. 13, 2014

Related U.S. Application Data

(63) Continuation of application No. 13/100,424, filed on May 4, 2011, now Pat. No. 8,590,364.

(60) Provisional application No. 61/370,282, filed on Aug. 3, 2010.

(51) Int. Cl.
*G01N 33/497* (2006.01)
*B60K 28/06* (2006.01)

(52) U.S. Cl.
CPC .......... *B60K 28/063* (2013.01); *G01N 33/4972* (2013.01)

(58) Field of Classification Search
CPC ... G01N 33/497; G01N 33/4972; A61B 5/097

USPC .......................................................... 73/23.3
See application file for complete search history.

(56) References Cited

U.S. PATENT DOCUMENTS

| | | | |
|---|---|---|---|
| 4,749,553 A * | 6/1988 | Lopez ................ | G01N 33/4972 180/272 |
| 5,020,628 A | 6/1991 | Bigliardi et al. | |
| 5,065,604 A | 11/1991 | Pattock | |
| 6,229,908 B1 | 5/2001 | Edmonds, III et al. | |

(Continued)

OTHER PUBLICATIONS

Breathalyzer—Wikipedia, the free encyclopedia, http://en.wikipedia.org/wiki/Breathalyzer, printed Apr. 30, 2011, 11 pages.

(Continued)

*Primary Examiner* — Hezron E Willliams
*Assistant Examiner* — Rodney T Frank
(74) *Attorney, Agent, or Firm* — Luis M. Ortiz; Kermit D. Lopez; Ortiz & Lopez, PLLC

(57) ABSTRACT

A breath alcohol ignition interlock device includes a mock beverage housing including at least one of breath alcohol electronics and a hand held breath alcohol analyzer therein, a mouthpiece in fluid communication with an alcohol sensor associated with the at least one of breath alcohol electronics and a hand held breath alcohol analyzer and a vent exhausting breath from the mock beverage housing. The mock beverage container housing can be disguised as a coffee cup, a fountain drink cup, a soda can, and a soft drink bottle. The mouthpiece can be disguised as a coffee cup lid, a fountain drink cup straw, a soda can opening, and a soft drink bottle top. A wireless communication module can support data synchronization and communications between the device and a base station installed within a motor vehicle.

20 Claims, 7 Drawing Sheets

(56) References Cited

U.S. PATENT DOCUMENTS

| | | | |
|---|---|---|---|
| 6,853,956 B2 | 2/2005 | Ballard, Jr. et al. | |
| 7,204,335 B2 * | 4/2007 | Stewart | G01N 33/4972 180/272 |
| 7,287,617 B2 | 10/2007 | Mobley et al. | |
| 7,341,693 B2 | 3/2008 | Der Ghazarian et al. | |
| 7,413,047 B2 | 8/2008 | Brown et al. | |
| 7,451,852 B2 * | 11/2008 | Stewart | B60K 28/063 180/272 |
| 7,797,982 B2 | 9/2010 | Burke et al. | |
| 8,336,665 B1 * | 12/2012 | Saunders | B60K 28/063 180/272 |
| 8,418,796 B2 * | 4/2013 | Flores | B60R 13/0275 180/272 |
| D700,531 S * | 3/2014 | Saunders | D10/81 |
| 8,701,814 B2 * | 4/2014 | Saunders | B60K 28/063 180/272 |
| 2007/0144812 A1 * | 6/2007 | Stewart | B60K 28/063 180/272 |
| 2007/0273537 A1 | 11/2007 | Crespo et al. | |
| 2010/0012417 A1 | 1/2010 | Walter et al. | |
| 2010/0063408 A1 | 3/2010 | Nothacker et al. | |
| 2011/0084820 A1 | 4/2011 | Walter et al. | |
| 2012/0048753 A1 * | 3/2012 | Johnson-Griggs | G01D 11/245 206/305 |
| 2012/0234708 A1 * | 9/2012 | Chabot | B60R 11/02 206/320 |
| 2013/0062232 A1 * | 3/2013 | Saunders | B60K 28/063 206/305 |
| 2014/0128760 A1 * | 5/2014 | Saunders | A61B 5/082 600/532 |

OTHER PUBLICATIONS

Ignition interlock device—Wikipedia, http://en.wikipedia.org/ignition_interlock_device, printed Apr. 30, 2011, 3 pages.

In-Hom—Your Alcohol Monitoring Alternative, Smart Start Ignition Systems—Breath Alcohol Ignition Interlock Devices (BAIIDs), http://www.smartstartinc.com/, printed Apr. 30, 2011, 1 page.

Taylor, L., "State of the Art Breathalyzers: A History," http://www.azduiatty.com/state-of-the-art-breathalyzers-a-history.htm, printed Apr. 30, 2011, 3 pages.

\* cited by examiner

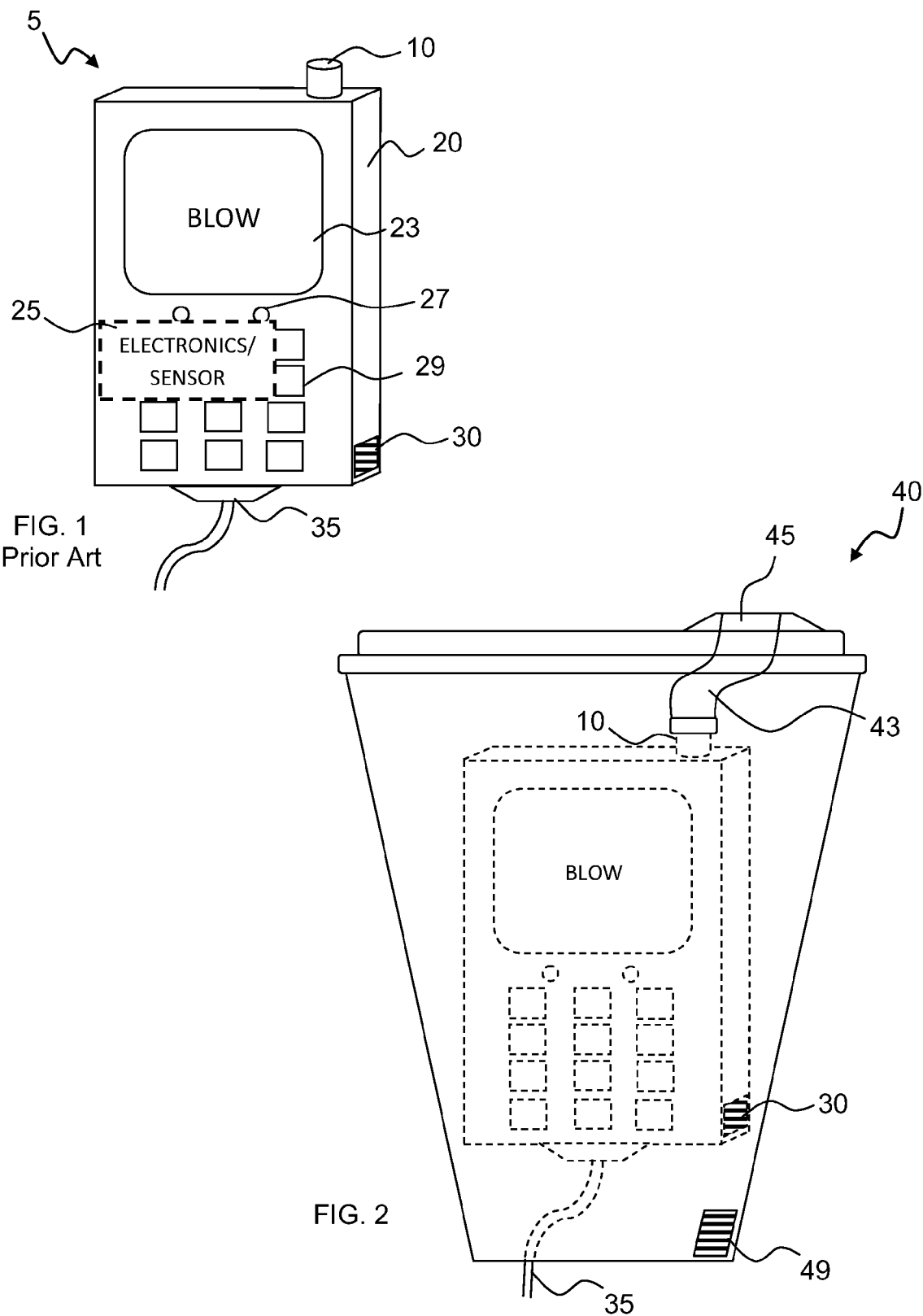

BEVERAGE DISGUISE FOR HAND HELD BREATHALYZER INTERFACE OF IGNITION INTERLOCK DEVICE

CROSS-REFERENCE TO PROVISIONAL APPLICATION

This patent application is a continuation of U.S. patent application Ser. No. 13/100,424, filed on May 4, 2011, and claims the benefit under 35 U.S.C. §119(e) of U.S. Provisional Application Ser. No. 61/370,282, entitled "Beverage Disguise for Hand Held Breathalyzer Interface of Ignition Interlock Device," which was filed on Aug. 3, 2010 and is incorporated herein by reference in its entirety. U.S. patent application Ser. No. 13/100,424 therefore claims priority to the Aug. 3, 2010 filing date of U.S. Provisional Application Ser. No. 61/370,282.

FIELD OF THE INVENTION

Embodiments are related to alcohol breathalyzers and ignition interlock systems. More particularly, embodiments are related to a disguise in the form of a mock non-alcoholic beverage (e.g., coffee cup, soda can, bottle soft drink) designed to accept the hand held breath analyzer therein and thereby disguising the hand held breath analyzer.

BACKGROUND

An ignition interlock device or a breath alcohol ignition interlock device (IID and BIID) is a breathalyzer (breath analyzer) installed on or around the dashboard of a vehicle, often as required by law following a DUI conviction. The ignition interlock device prevents a vehicle from starting until the driver successfully passes a blood alcohol concentration test. Before the vehicle will start, the driver must blow into the BAC tester. If the breath test shows a driver's BAC to be above a set limit, usually around 0.02-0.04%, the starter on the car vehicle will lock and the driver can't use the vehicle. If a driver's BAC is below that level, then the vehicle will start and operate normally.

IIDs are often issued as part of the mandatory punishment for a DUI/DWI conviction. A single DUI conviction could require that one of these systems be installed in the offender's car. If required by the court of law as part of a conviction or plea bargain, the DUI offender will also be responsible for paying for the installation and monthly usage fees for the devices, which may cost hundreds of dollars. Alcohol detection devices can also include a camera to record the user of the system during its use and ensure that a driver is using the system. Wireless (cellular) reporting to remote monitoring stations is also being promoted and suggested for state adoption by breathalyzer system manufacturing companies.

Although breathalyzer systems can ensure public safety and deter future offenses by DUI offenders, their installation, albeit temporary, is unsightly and can be embarrassing to offenders. Many DUI offenders feel remorseful about the offense, willingly comply with terms of conviction or a plea that includes breathalyzer use and are otherwise law-abiding citizens. Compliance with breathalyzer usage to ensure sober vehicle operation is the only written purpose by states and municipality that legally require the installation of such systems in offender vehicles. Public embarrassment of offenders (especially first offenders), however, is not affirmatively written into legislation for jurisdictions mandating the use of breathalyzer systems.

For the foregoing reasons, the present inventor believes that DUI offenders that are required to pay for the installation and use of ignition interlock devices should also be able to disguise the user interface portion of such systems during a court-mandated period of use.

SUMMARY

The following summary is provided to facilitate an understanding of some of the innovative features unique to the disclosed embodiment and is not intended to be a full description. A full appreciation of the various aspects of the embodiments disclosed herein can be gained by taking the entire specification, claims, drawings, and abstract as a whole.

The present inventor proposes a disguise in the form of a mock non-alcoholic beverage (e.g., coffee cup, soda can, soft drink bottle) designed to hold at least one of integrated breath analyzer electronics or a hand held breath analyzer therein, thereby disguising the hand held breath analyzer as a beverage. The disguise can also be referred to herein for convenience as "breathalyzer disguise".

In accordance with an aspect of the disclosed embodiments, the breathalyzer disguise is provided as a mock beverage container such as a disposable coffee cup, fountain beverage cup, soda can or soft drink bottle that can accept and hold a hand held interlace of a breathalyzer ignition interlock system therein.

In accordance with another aspect of the disclosed embodiments, the breathalyzer disguise can include a mouthpiece in fluid connection with a breath capture/input of a handheld interface for a breathalyzer ignition interlock system to accept breath from a user for analysis by the breathalyzer ignition interlock system.

In accordance with yet another aspect of the disclosed embodiments, the breathalyzer disguise can include exhaust vents therein allowing analyzed breath exiting the hand held interface of a breathalyzer ignition interlock interface to exit.

In accordance with another aspect of the disclosed embodiments, the breathalyzer disguise can be provided in a clamshell format to accept a hand held interlace of a breathalyzer ignition interlock system.

In accordance with another aspect of the disclosed embodiments, a breathalyzer ignition interlock system can be provided with wireless communication capability and be provided in the form of a mock beverage container disguise.

In accordance with another aspect of the disclosed embodiments, a wireless breathalyzer ignition interlock system disguised as a beverage container can communicate with a base station installed within a motor vehicle.

In accordance with another aspect of the disclosed embodiments, a wireless breathalyzer ignition interlock system disguised as a beverage container can communicate with a base station installed within a motor vehicle using Bluetooth wireless communications.

In accordance with another aspect of the disclosed embodiments, a wireless breathalyzer ignition interlock system disguised as a beverage container can be synchronized with and can communicate with an assigned base station installed within a motor vehicle.

In accordance with another aspect of the disclosed embodiments, a wireless breathalyzer ignition interlock system disguised as a beverage container can be synchronized with and can communicate with an assigned base station installed within a motor vehicle using Bluetooth wireless communications.

The aforementioned aspects and other objectives and advantages can now be achieved as described herein. A breath alcohol ignition interlock device can comprise a mock beverage housing including at least one of breath alcohol electronics and a hand held breath alcohol analyzer therein, a mouthpiece in fluid communication with an alcohol sensor associated with the at least one of breath alcohol electronics and a hand held breath alcohol analyzer, and a vent exhausting breath from the mock beverage housing.

In another embodiment, the mock beverage container housing can be provided in the disguise of at least one of, for example, a coffee cup, a fountain drink cup, a soda can, a soft drink bottle, and so forth, thereby disguising the hand held breath analyzer as a beverage container.

In another embodiment, the mouthpiece can be provided in the disguise of at least one of: a coffee cup lid, a fountain drink cup straw, a soda can opening, a soft drink bottle top.

In yet another embodiment, the mock beverage container housing accepts and holds therein a hand held interface of a breathalyzer ignition interlock device. In still another embodiment, the mock beverage container housing can be provided in the disguise of at least one of, for example, a coffee cup, a fountain drink cup, a soda can, a soft drink bottle, thereby disguising the hand held breath analyzer as a beverage container.

In another embodiment, the mouthpiece can be provided in the disguise of at least one of: a coffee cup lid, a fountain drink cup straw, a soda can opening, a soft drink bottle top.

In other embodiments, the mouthpiece can be in fluid connection with a second mouthpiece associated with said handheld interface of a breathalyzer ignition interlock device.

In still other embodiments, the exhaust allows analyzed breath exiting the hand held interface of a breathalyzer ignition interlock interface to exit.

In still other embodiments, the mouthpiece can be in fluid connection with a second mouthpiece associated with said handheld interface of a breathalyzer ignition interlock device.

In another embodiment, the exhaust allows analyzed breath exiting the hand held interface of a breathalyzer ignition interlock interface to exit. In another embodiment, a wireless communication module can support communication with a base station installed within a motor vehicle.

In still another embodiment, the wireless communication module can comprise a Bluetooth wireless communications module.

In still further embodiments, the Bluetooth wireless communications module can support data synchronization and communications with said base station.

BRIEF DESCRIPTION OF THE FIGURES

The accompanying figures, in which like reference numerals refer to identical or functionally similar elements throughout the separate views and which are incorporated in and form a part of the specification, further illustrate the disclosed embodiments and, together with the detailed description herein, serve to explain the principles of the disclosed embodiments.

FIG. 1 labeled as "prior art" illustrates a hand held interface of a typical IID;

FIG. 2 illustrates an IID housing disguise in the form of a beverage container, in accordance with the disclosed embodiments;

DETAILED DESCRIPTION

Figure 3:
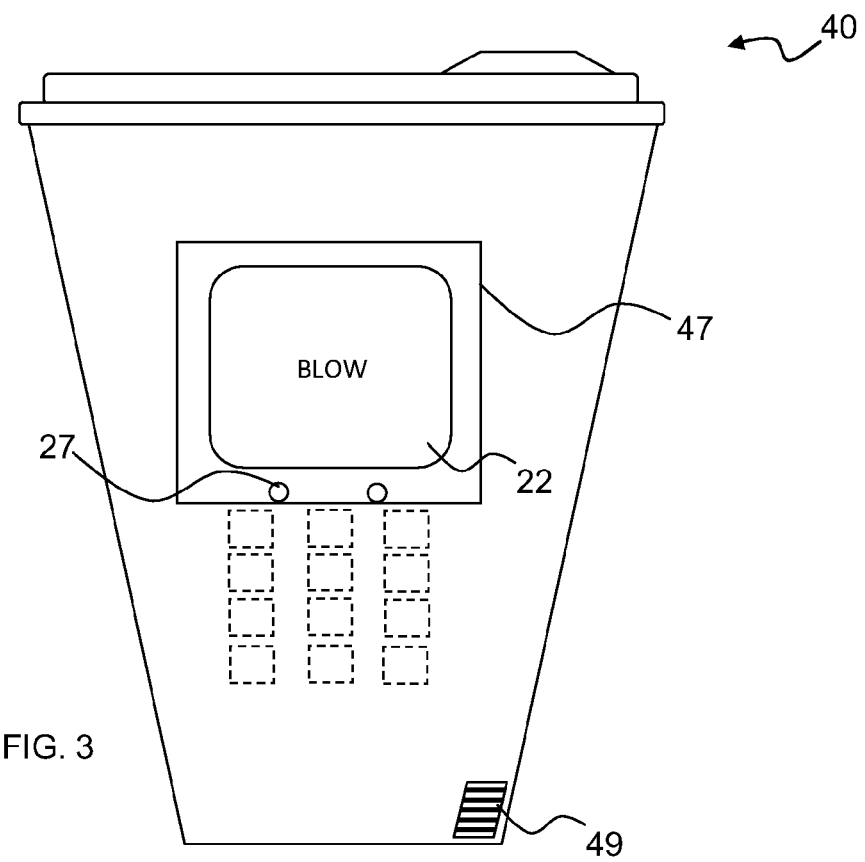
FIG. 3 illustrates an IID housing disguise holding/containing the hand held user interface of an IID therein and including a window cut into the side of IID housing disguise to allow users to see the display screen and status indicator lights disposed on the enclosed hand held user interface, in accordance with the disclosed embodiments.

The particular values and configurations discussed in these non-limiting examples can be varied and are cited merely to illustrate one or more embodiments and are not intended to limit the scope thereof.

A beverage disguise for hand held breathalyzer interface of ignition interlock system can be provided in the form of a non-alcoholic beverage container. The non-alcoholic beverage container can be provided in the form of a mock, disposable coffee cup, paper cup, and soda can or soft drink bottle.

Referring to FIG. 1, which is labeled as "prior art", a hand held user interface 5 of a typical breathalyzer and ignition interlock system is illustrated. The hand held user interface 5 includes a mouthpiece 10, a housing 20 connected to the mouthpiece 10 to accept user breath, a display screen 23, status indicator lights 27, alcohol analyzing electronics and sensors 25 to analyze user breath alcohol content, a vent 30 to exhaust user breath passing through the housing 20 for analysis, and wired connection 35 to an control module (e.g., vehicle base station) installed within a motor vehicle for controlling vehicle ignition.

Modern ignition interlock devices use an ethanol-specific fuel cell for a sensor. A fuel cell sensor is an electrochemical device in which alcohol undergoes a chemical oxidation reaction at a catalytic electrode surface (platinum) to generate an electric current. This current is then measured and converted to an alcohol equivalent reading. Although fuel cell technology is not as accurate or reliable for a sensor as infrared spectroscopy technology used in evidentiary breathalyzers, they are cheaper and tend to be more specific for alcohol. The devices keep a record of the activity on the device and the interlocked vehicle's electrical system. This record, or log, is printed out or downloaded each time the device's sensors are calibrated, commonly at 30, 60, or 90-day intervals. Authorities may require periodic review of the log. If violations are detected, then additional sanctions can be implemented. Periodic calibration is performed using either a pressurized alcohol-gas mixture at a known alcohol concentration, or with an alcohol wet bath arrangement that contains a known alcohol solution.

The costs of installation, maintenance, and calibration are generally paid by the offender, and typically are about $75 per month. In the United States, the National Highway Traffic Safety Administration's NHTSA Conforming Products List maintains a list of federally approved IID devices. Many countries are requiring the ignition interlock as a penalty for drivers convicted of driving under the influence, especially repeat offenders. Most U.S. states now permit judges to order the installation of an IID as a condition of probation for repeat offenders, and for first offenders in some states, law may mandate installation.

FIG. 2 illustrates an IID housing disguise 40 provided in the form of a beverage container. The IID housing disguise 40 can accept the hand held user interface 5 of an IID. The IID housing disguise 40 includes an IID housing disguise mouthpiece interface 45 and an IID housing disguise vent 49. The IID housing disguise mouthpiece interface 45 can be placed in fluid connection 43 to a mouthpiece 10 of a hand held user interface 5. The IID housing disguise vent 49 can allow breath exhausted from the vent 30 of the hand held interface contained in the IID housing disguise 40 to also exhaust from the IID housing disguise 40. Wired connection 35 can also be achieved through an open bottom of the IID housing disguise 40.

FIG. 3 illustrates an IID housing disguise 40 holding/containing the hand held user interface 5 of an IID therein and including a window 47 cut into the side of an IID housing disguise 40 to allow users to see the display screen 22 and status indicator lights 27 disposed on the enclosed hand held user interface 5.

Figure 4:
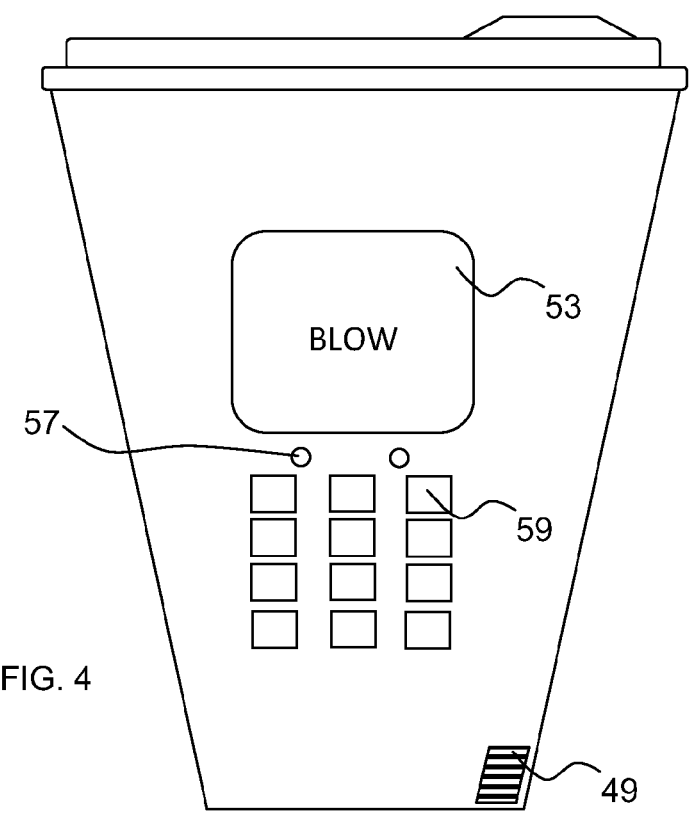
FIG. 4 illustrates an IID housing disguise holding/containing breath analyzing functionality of an IID therein and including a display screen and status indicator lights integrated into the side of an IID housing disguise to allow users to see the commands on the display screen and of status indicator lights disposed on the IID housing, in accordance with the disclosed embodiments.

FIG. 4 illustrates an IID housing disguise 40 holding/containing breath analyzing functionality of an IID therein and including a display screen 53 and status indicator lights 57 integrated into the side of IID housing disguise 40 to allow users to see the commands on the display screen 53 and of status indicator lights 57 disposed on the IID housing 40. A user interface 59 can also be integrated into the side of IID housing 40 to allow a user to operate the IID.

Figure 5:
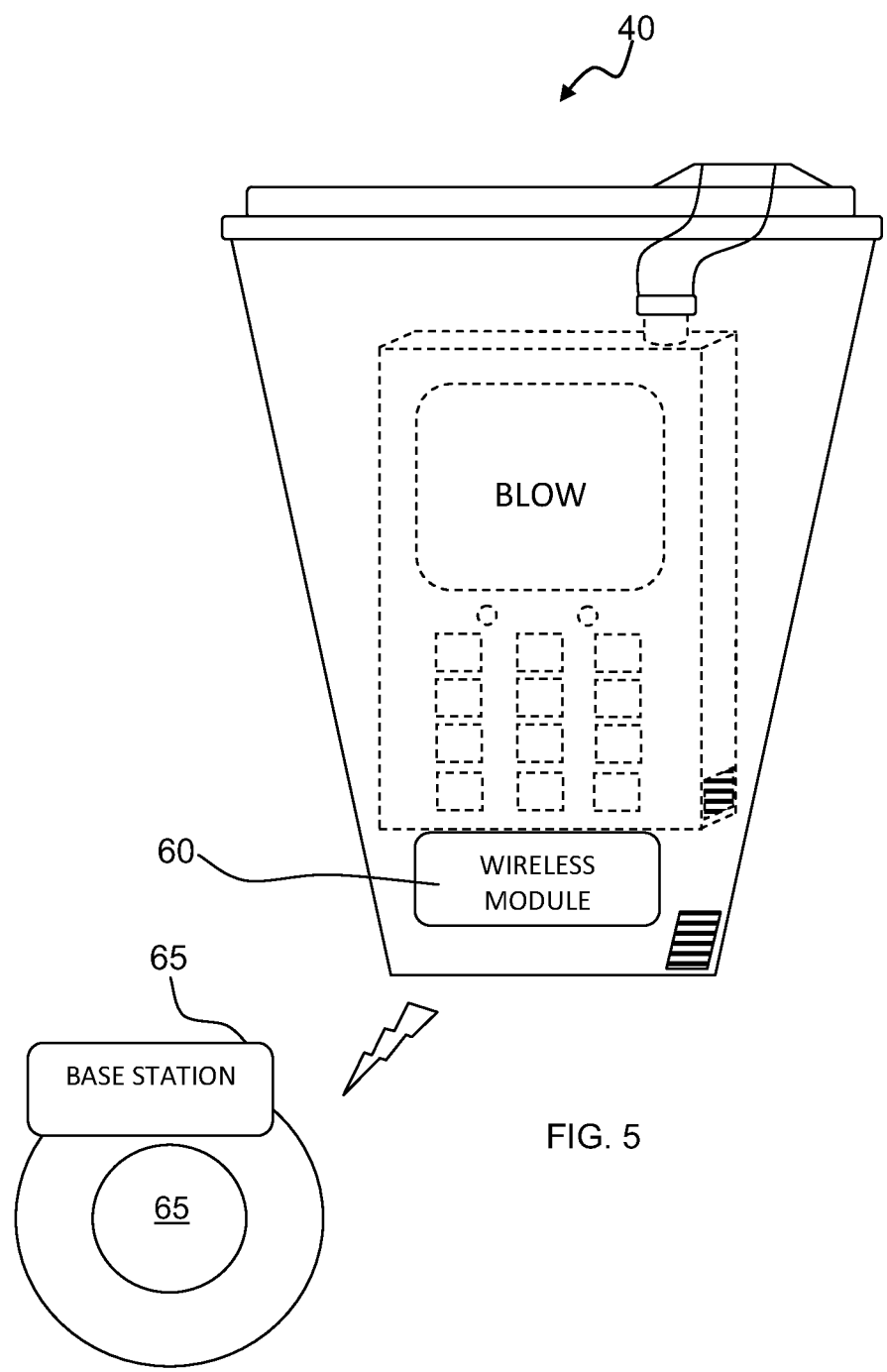
FIG. 5 illustrates an IID housing disguise including a wireless communications module, in accordance with the disclosed embodiments.

It should be appreciated that communications can be maintained between the IID 40 and a base station 65 using wired communications 35 or wireless communications 60. Referring to FIG. 5, an IID housing disguise 40 is illustrated that includes a wireless communications module 60. Wireless communication module 60 can support wireless communication with a base station 65 installed within a motor vehicle associated with the IID 40. The wireless communication module 60 can be a Bluetooth wireless communications module to support data synchronization and communications between the IID 40 and the base station 65.

Figure 6:
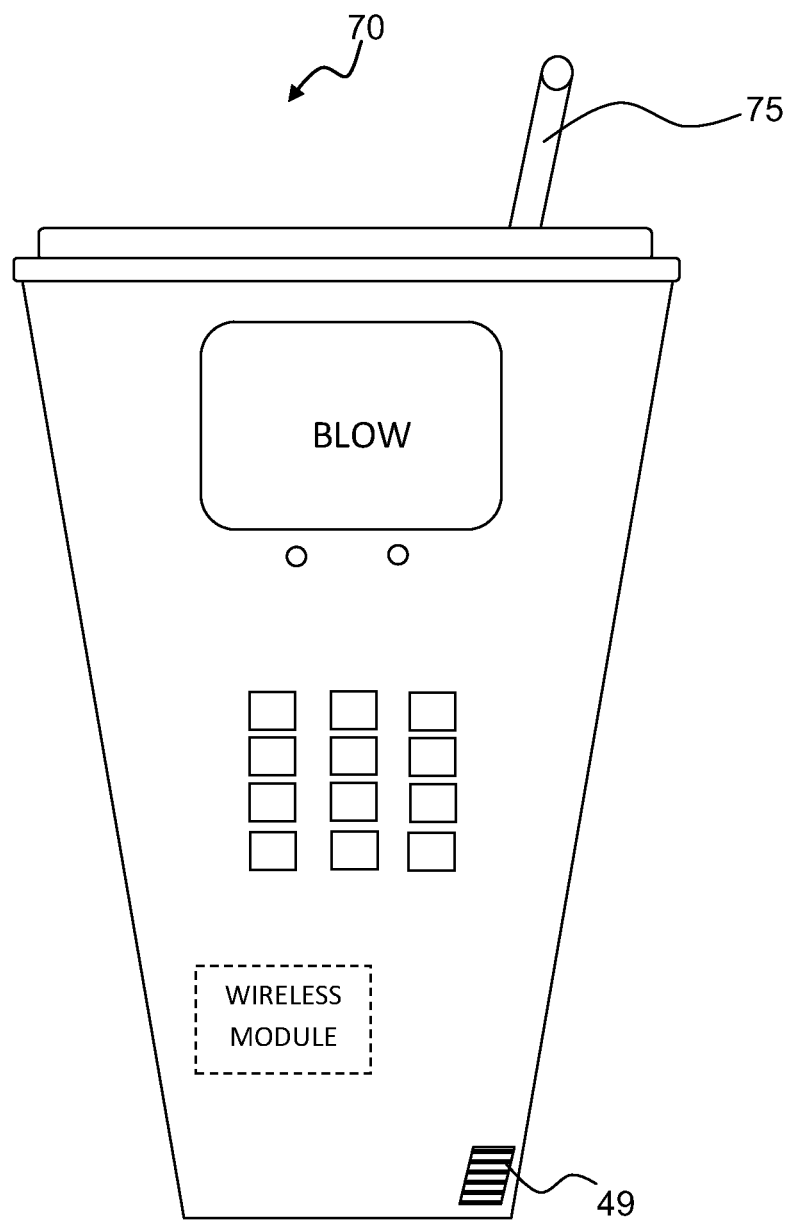
FIG. 6 illustrates an IID provided in the form of a beverage cup that includes a straw as the IID mouthpiece, in accordance with the disclosed embodiments.

FIG. 6 illustrates an IID 70 provided in the form of a beverage cup that includes a straw 75 as the IID mouthpiece. The straw 75 can be used by a user to blow into the IID 70. As also explained in FIG. 2, it should be appreciated that the straw 75 can be placed into fluid communication with mouthpiece 10 on an IID 40 that is being held within the IID 70. The IID 70 can also include a vent 49 for the exhaust of breath that is placed into the device by straw 75.

Figure 7:
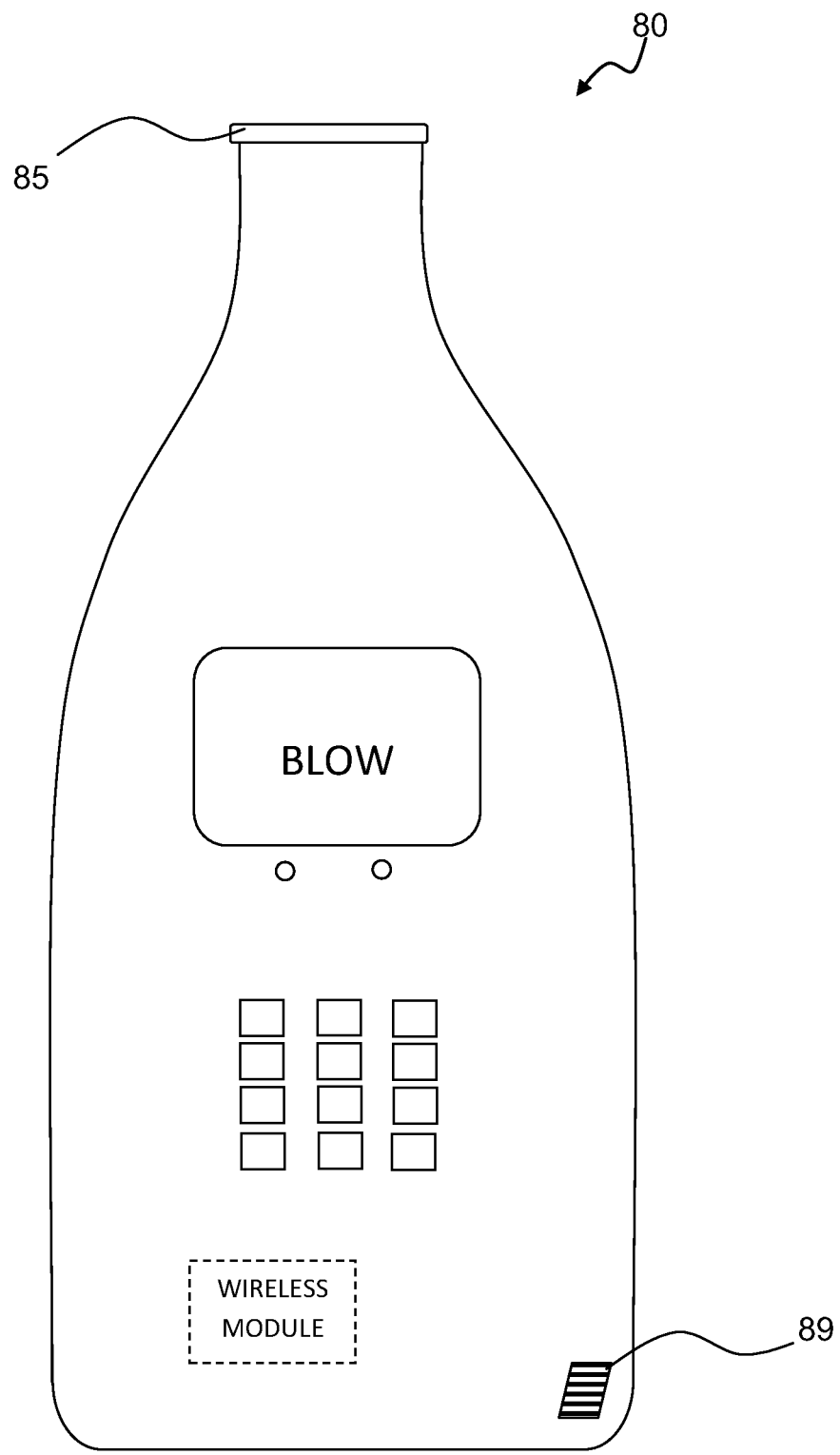
FIG. 7 illustrates an IID provided in the form of a beverage bottle that includes an opening as the IID mouthpiece, in accordance with the disclosed embodiments.

FIG. 7 illustrates an IID 80 provided in the form of a beverage bottle that includes an opening 85 as the IID mouthpiece. The opening 85 can be used by a user to blow into the IID 80. As also explained in FIGS. 2 and 6, it should be appreciated that the opening 85 can be placed into fluid communication with a mouthpiece 10 that can be carried inside the bottle-like IID 80. The IID 80 can also include a vent 89 for the exhaust of breath that is placed into the device by opening 85.

Figure 8:
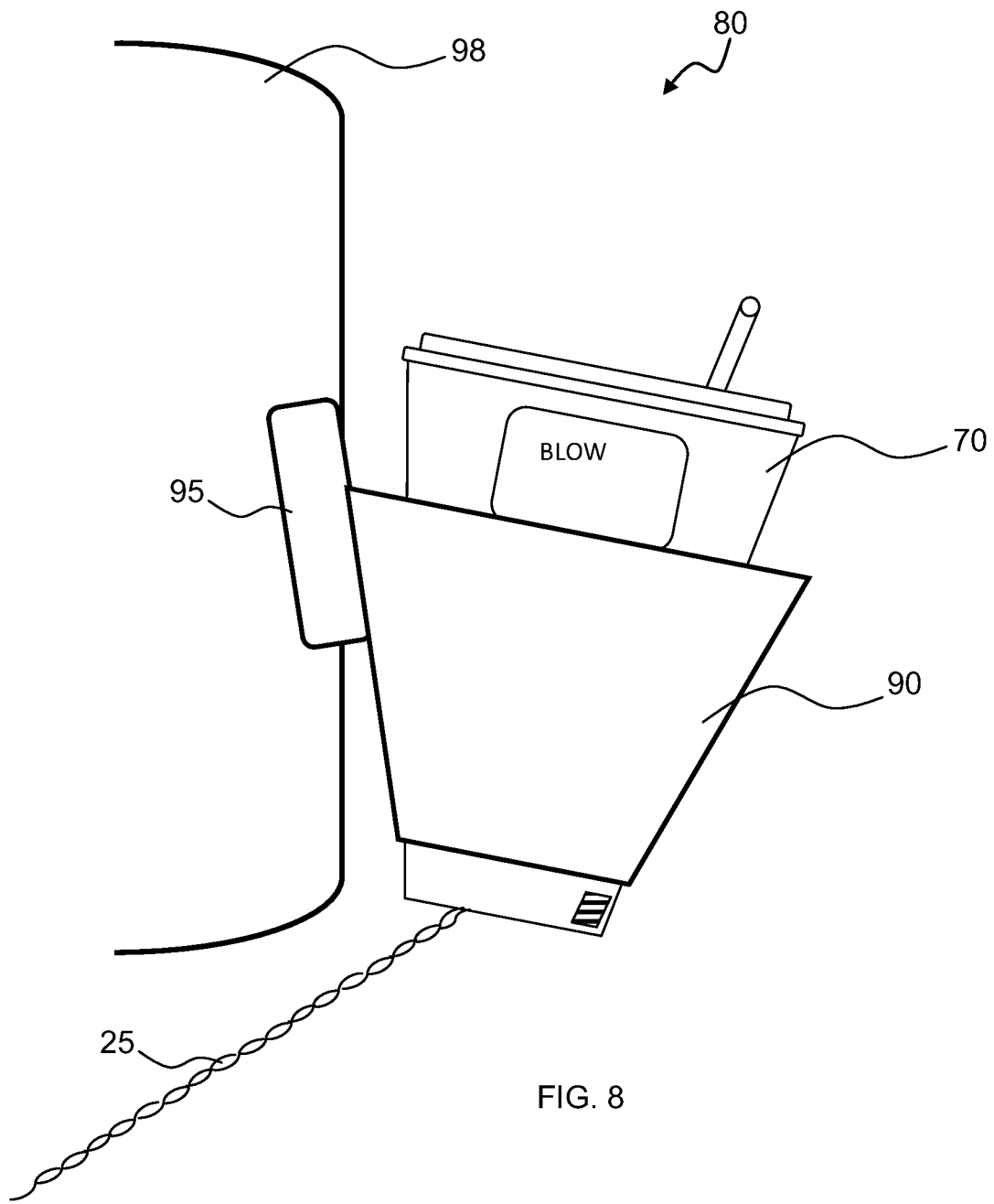
FIG. 8 illustrates a cup holder that can be provided to hold/support an IID beverage-housing disguise, in accordance with the disclosed embodiments.

FIG. 8 illustrates a cup holder 90 that can be provided to hold/support an IID beverage-housing disguise 70. The cup holder 90 can be mounted at a base 95 to a dashboard 98 of an associated motor vehicle. The cup holder 90 can safely hold an IID 70 while it is not in use. When used, wiring 25 is shown connecting the IID 70 with a base station mounted to a vehicle. Otherwise communications with a base station can be wireless as described in detail above.

Figure 9:
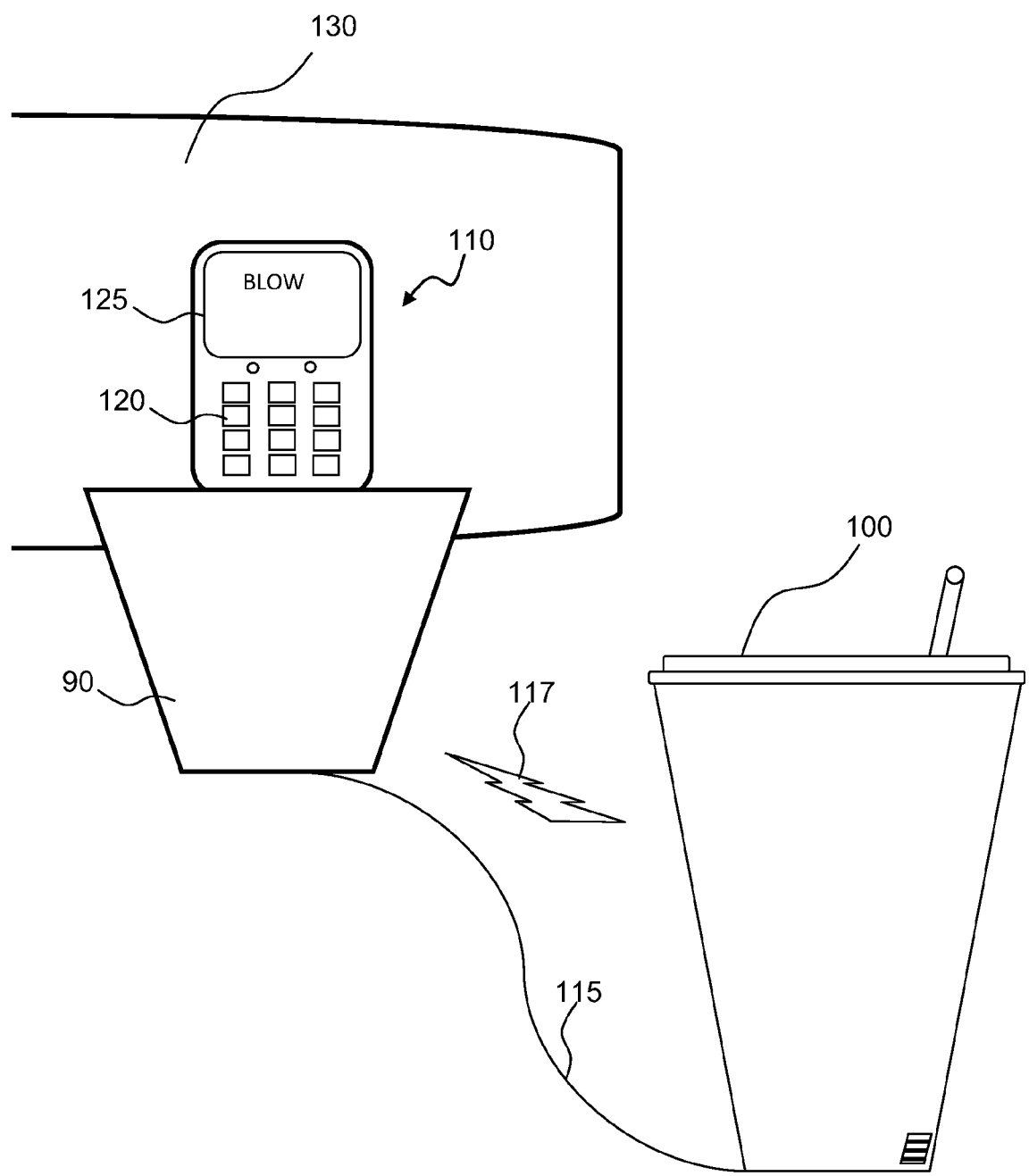
FIG. 9 illustrates a schematic diagram of an IID system wherein an IID housing device communicates either wired or wirelessly with a user interface and display mounted remotely on a vehicle dashboard, in accordance with the disclosed embodiments.

FIG. 9 illustrates a schematic diagram of an IID system wherein an IID beverage housing disguise 100 can communicate either wired 115 or wirelessly 117 with a user interface 110 including keyboard 120 and display 125 mounted remotely on a vehicle dashboard 130. The user interface 110 can also be incorporated with the cup holder 90. It should be appreciated now given the foregoing description that the display 125 and functions keys 120 for an IID system do not have to be integrated directly into the hand held user interface associated with the mouthpiece used to access user breath. Directions and user inputs (other than breath specimen) can be provided on the remote user interface. Such an arrangement can also improve safety during vehicle operation.

Based on the foregoing, it can be appreciated that various embodiments and alternative embodiments can be implemented. For example, in one embodiment a breath alcohol ignition interlock device can comprise a mock beverage housing including at least one of breath alcohol electronics and a hand held breath alcohol analyzer therein; a mouthpiece in fluid communication with an alcohol sensor associated with the at least one of breath alcohol electronics and a hand held breath alcohol analyzer; and a vent exhausting breath from the mock beverage housing. In another embodiment, the mock beverage container housing can be provided in the disguise of at least one of, for example, a coffee cup, a fountain drink cup, a soda can, a soft drink bottle, and so forth, thereby disguising the hand held breath analyzer as a beverage container. In another embodiment, the mouthpiece can be provided in the disguise of at least one of: a coffee cup lid, a fountain drink cup straw, a soda can opening, a soft drink bottle top. In yet another embodiment, the mock beverage container housing accepts and holds therein a hand held interface of a breathalyzer ignition interlock device. In still another embodiment, the mock beverage container housing can be provided in the disguise of at least one of, for example, a coffee cup, a fountain drink cup, a soda can, a soft drink bottle, thereby disguising the hand held breath analyzer as a beverage container.

In another embodiment, the mouthpiece can be provided in the disguise of at least one of: a coffee cup lid, a fountain drink cup straw, a soda can opening, a soft drink bottle top. In other embodiments, the mouthpiece can be in fluid connection with a second mouthpiece associated with said handheld interface of a breathalyzer ignition interlock device. In still other embodiments, the exhaust allows analyzed breath exiting the hand held interface of a breathalyzer ignition interlock interface to exit. In still other embodiments, the mouthpiece can be in fluid connection with a second mouthpiece associated with said handheld interface of a breathalyzer ignition interlock device. In another embodiment, the exhaust allows analyzed breath exiting the hand held interface of a breathalyzer ignition interlock interface to exit. In another embodiment, a wireless communication module can support communication with a base station installed within a motor vehicle. In still another embodiment, the wireless communication module can comprise a Bluetooth wireless communications module. In still further embodiments, the Bluetooth wireless communications module can support data synchronization and communications with said base station.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A disguise for an ignition interlock device wherein a mouthpiece is coupled to the ignition interlock device, the disguise comprising:
a mock beverage container comprising an integrated bottom having a lower hole and an opening opposite the integrated bottom, wherein the ignition interlock device fits inside the mock beverage container and the opening provides access to the mouthpiece when the ignition interlock device is inside the mock beverage container; and
a removable lid removably attachable to the mock beverage container at the opening to thereby hold the ignition interlock device inside the mock beverage container while providing access to the mouthpiece when the ignition interlock device is contained inside the mock beverage container.

2. The disguise for ignition interlock devices of claim 1, wherein the mock beverage container includes a side and has a window cut into the side to facilitate user viewing of, access to, and control of the ignition interlock device.

3. The disguise for ignition interlock devices of claim 1, wherein the mock beverage container is provided in a disguise of at least one of: a coffee cup, a fountain drink cup, a soda can, a soft drink bottle.

4. The disguise for ignition interlock devices of claim 2, wherein the mock beverage container is provided in a disguise of at least one of: a coffee cup, a fountain drink cup, a soda can, a soft drink bottle.

5. The disguise for ignition interlock devices of claim 3, wherein the mock beverage container includes a side and has a window cut into the side to facilitate user access to at least one of a display screen and controls integrated in the ignition interlock device.

6. The disguise for ignition interlock devices of claim 1, wherein the lower hole is operable as a pass-through for a cord connected to the ignition interlock device.

7. The disguise for ignition interlock devices of claim 1, wherein the lower hole provides passage out of the disguise of breath blown into the mouthpiece for processing by a breath alcohol sensor associated with the ignition interlock device.

8. The disguise for ignition interlock devices of claim 2, wherein the lower hole is operable as a pass-through for a cord connected to the ignition interlock device.

9. The disguise for ignition interlock devices of claim 2, wherein the lower hole provides passage out of the disguise of breath blown into the mouthpiece for processing by a breath alcohol sensor associated with the ignition interlock device.

10. A disguise for an ignition interlock device wherein a mouthpiece is coupled to the ignition interlock device, the disguise comprising: a mock beverage container comprising an integrated bottom having a lower hole and an opening opposite the integrated bottom, wherein the ignition interlock device fits inside the mock beverage container and the opening provides access to the mouthpiece when the ignition interlock device is inside the mock beverage container, and wherein the lower hole provides for at least one of a cord connected to the ignition interlock device body and passage out of the disguise of breath blown into the mouthpiece; and a removable lid removably attachable to the mock beverage container at the opening to thereby hold the ignition interlock device inside the mock beverage container while providing access to the mouthpiece when the ignition interlock device is contained inside the mock beverage container.

11. The disguise for ignition interlock devices of claim 10, wherein the mock beverage container includes a side and has a window cut into the side to facilitate user viewing of, access to, and control of the ignition interlock device.

12. The disguise for ignition interlock devices of claim 10, wherein the mock beverage container is provided in a disguise of at least one of: a coffee cup, a fountain drink cup, a soda can, a soft drink bottle.

13. The disguise for ignition interlock devices of claim 11, where n the mock beverage container is provided in a disguise of at least one of: a coffee cup, a fountain drink cup, a soda can, a soft drink bottle.

14. The disguise for ignition interlock devices of claim 12, wherein the mock beverage container includes a side and has a window cut into the side to facilitate user access to at least one of a display screen and controls integrated in the ignition interlock device.

15. A disguise for an ignition interlock device wherein a mouthpiece is coupled to: the ignition interlock device, the disguise comprising: a mock beverage container comprising a side, an integrated bottom and an opening opposite the integrated bottom, wherein the integrated bottom has a lower hole, wherein an ignition interlock device fits inside the :mock beverage container and the opening provides access to the mouthpiece when the ignition interlock device is inside the mock beverage container; and a removable lid having an access hole, wherein the opening is configured to hold the removable lid, the lid holds the ignition interlock device inside the mock beverage container, and the access hole provides access to the mouthpiece.

16. The disguise for ignition interlock devices of claim 15, wherein said hole formed on the bottom is operable as at least one of a pass-through for a cord connected to the ignition interlock device and an exhaust for releasing from the mock beverage container human breath blown into the mouthpiece of the ignition interlock device concealed by the mock beverage container for processing by a breath alcohol sensor associated with the ignition interlock device.

17. The disguise for ignition interlock devices of claim 15, wherein a second mouthpiece is integrated onto said removable lid at the access hole as is adapted for placement into fluid connection with the mouthpiece coupled to the ignition interlock device.

18. The disguise for ignition interlock devices of claim 15, wherein the mock beverage container includes a side and has a window cut into the side to facilitate user viewing of, access to, and control of the ignition interlock device.

19. The disguise for ignition interlock devices of claim 16, wherein a second mouthpiece is integrated onto said removable lid at the access hole as is adapted for placement into fluid connection with the mouthpiece coupled to the ignition interlock device.

20. The disguise for ignition interlock devices of claim 19, wherein the second mouthpiece is provided in disguise of at least one of: a coffee cup lid, a fountain drink cup straw, a soda can opening, a soft drink bottle top.

* * * * *